United States Patent [19]

Upeslacis et al.

[11] 4,440,758

[45] Apr. 3, 1984

[54] POLY-CATION SALTS OF BIS(OR TRIS)[4-O-MONOHEXOSE-OXY]-ARYLENE SULFATE DERIVATIVES

[75] Inventors: Janis Upeslacis, Pomona, N.Y.; Robert E. Schaub, Upper Saddle River, N.J.; Seymour Bernstein, New City, N.Y.

[73] Assignee: American Cyanamid Company, Stamford, Conn.

[21] Appl. No.: 436,208

[22] Filed: Oct. 25, 1982

[51] Int. Cl.$^3$ .................. A61K 31/70; C07H 15/22
[52] U.S. Cl. .................. 424/180; 536/4.1; 536/17.2; 536/17.6; 536/17.9; 536/18.5; 536/18.6; 536/118; 536/122

[58] Field of Search ............. 424/180; 536/4.1, 17.2, 536/17.6, 17.9, 18.5, 18.4, 18.6, 18.7, 118, 122

[56] References Cited

U.S. PATENT DOCUMENTS

| | | | |
|---|---|---|---|
| 2,235,788 | 3/1941 | White | 536/18.4 |
| 4,120,954 | 10/1978 | Joseph et al. | 536/118 |
| 4,243,653 | 1/1981 | Sovak et al. | 536/18.7 |
| 4,337,249 | 6/1982 | Conrow et al. | 536/118 |

Primary Examiner—Johnnie R. Brown
Attorney, Agent, or Firm—Anne M. Rosenblum

[57] ABSTRACT

Poly-cation salts of bis(or tris)[4-O-monohexose-oxy]-arylene sulfate derivatives useful as modulators of the complement system, the intermediates thereof and the process of making such intermediates and products.

18 Claims, No Drawings

POLY-CATION SALTS OF BIS(OR TRIS)[4-O-MONOHEXOSE-OXY]-ARYLENE SULFATE DERIVATIVES

BACKGROUND OF THE INVENTION

1. Field of the Invention

The present invention relates to novel cation salts of bis(or tris) [4-O-monohexose-oxy]-arylene sulfate derivatives, to their use as modulators of the complement system of warm-blooded animals, to the intermediates thereof and to the process for the preparation of such intermediates and end products.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W. H. O. 39: 935 (1968); Annu. Rev. Med. 19: 1 (1968); Johns Hopkins Med. J. 128: 57 (1971); Harvey Lect. 66: 75 (1972); N. Engl. J. Med. 287: 452, 489, 545, 492, 642 (1972); Sci. Am. 229 (5): 54 (1973); Fed. Pro. 32: 134 (1973); Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant Rev.: 32 (1976); "Complement: Mechanisms and Functions," Prentice-Hall, Englewood Cliffs, N.J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1659 (1977); Harvey Lect. 72: 139 (1976–1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestions regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 115: 813 (1978); J. Biol. Chem. 254: 9908 (1979).

A variety of substances have been disclosed as inhibiting the complement system, i.e., as complement inhibitors. For example, the compounds, 3,3'-ureylenebis-[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, Br. J. Exp. Pathol. 33: 327 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem. 47: 547 (1969); J. Immunol. 104: 279 (1970); J. Immunol. 106: 241 (1971); J. Immunol. 111: 1061 (1973); Biochim. Biophys. Acta 317: 539 (1973); Life Sci. 13: 351 (1973); J. Immunol. 113: 584 (1974); Immunology 26: 819

(1974); J. Med. Chem. 17: 1160 (1974); Biochim. Biophys. Res. Comm. 67: 225 (1975); Ann. N.Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci. 66: 1367 (1977); Chem. Pharm. Bull. 25: 1202 (1977); Biochim. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979); Biochim. Biophys. Acta 611: 196 (1980); and J. Med. Chem. 23: 240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (Cl inhibitor), N. Engl. J. Med. 286: 808 (1972); 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosanpolysulfoester has an anticomplementary activity on human serum, both in vitro and in vivo, as judged by the reduction in total hemolytic complement activity, Pathol. Biol. 25: 33; 25 (2): 105; 25 (3): 179 (1977).

SUMMARY OF THE INVENTION

The instant invention relates to new compounds bis(or tris)[4-O-monohexose-oxy]-arylene sulfate derivatives and the cation salts thereof, that modulate the complement system, thereby modulating complement activity in body fluids. Moreover, this invention involves a method of modulating the complement system in a body fluid which comprises subjecting body fluid complement to the action of an effective complement modulating amount of the above-identified compounds. This invention further concerns a method of modulating the complement system in a warm-blooded animal which comprises administering to said animal an effective complement modulating amount of the above-identified compounds.

The invention also deals with the novel precursors that act as intermediates in preparing the abovedescribed complement modulating compounds of this invention.

DETAILED DESCRIPTION OF THE INVENTION

In accordance with the present invention, there are provided novel compounds represented by the following generic Formula I:

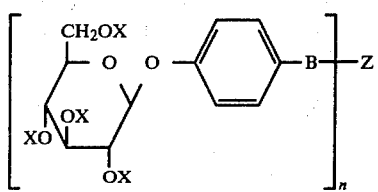

wherein X is $-SO_3M$ and M is a nontoxic pharmaceutically acceptable cation salt, wherein the salt forming moiety is selected from the group consisting of alkali metal, alkaline earth metal, aluminum, ammonia, zinc and substituted ammonia selected from the group consisting of trialkylamine ($C_1$-$C_6$), piperidine, pyrazine, alkanolamine ($C_2$-$C_6$) and cycloalkylamine ($C_3$-$C_6$); B is selected from the group consisting of $-NHCO-$ and $-NHSO_2-$; n is an integer 2 or 3; and Z is an arylene selected from the group consisting of:

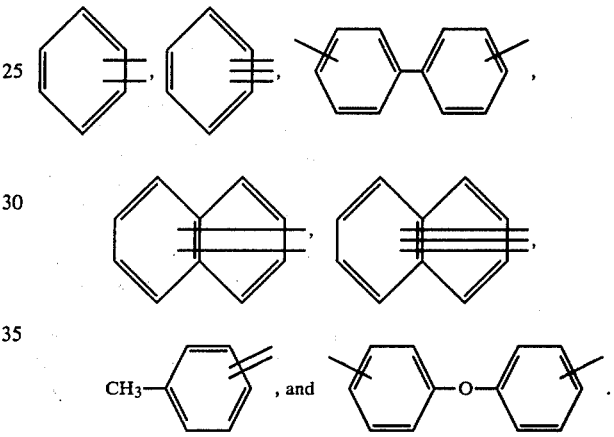

Particularly preferred compounds of Formula I which are of major interest as modulators of the complement system are dodecasodium N,N',N''-tris[4-[(2,3,4,6-tetra-O-sulfo-β-D-glucopyranosyl)oxy]-phenyl]-1,3,5-benzenetrisulfonamide and dodecatriethylammonium N,N',N''-tris[4-[(2,3,4,6-tetra-O-sulfo-β-D-glucopyranosyl)oxy]phenyl]-1,3,5-benzenetrisulfonamide Other representative compounds of Formula I include:

Dodecasodium N,N',N''-tris[4-[(2,3,4,6-tetra-O-sulfo-β-D-glucopyranosyl)oxy]phenyl]-1,3,5-benzenetricarboxamide Octasodium N,N'-bis[4-[(2,3,4,6-tetra-O-sulfo-β-D-glucopyranosyl)oxy]phenyl]-1,4-benzenedicarboxamide Octasodium N,N'-bis[4-[(2,3,4,6-tetra-O-sulfo-β-D-glucopyranosyl)oxy]phenyl]-4,4'-biphenyldisulfonamide Octasodium N,N'-bis[4-[(2,3,4,6-tetra-O-sulfo-β-D-glucopyranosyl)oxy]phenyl]-2,6-naphthalenedisulfonamide Dodecasodium N,N',N''-tris[4-[(2,3,4,6-tetra-O-sulfo-β-D-glucopyranosyl)oxy]phenyl]-1,3,6-naphthalenetrisulfonamide Octasodium N,N'-bis[4-[(2,3,4,6-tetra-O-sulfo-β-D-glucopyranosyl)oxy]phenyl]-3,5-toluenedisulfonamide Octasodium N,N'-bis[4-[(2,3,4,6-tetra-O-sulfo-β-D-glucopyranosyl)oxy]phenyl]-4,4'-dicarboxamidodiphenyl ether.

This invention further deals with a method of modulating the complement system in a body fluid, such as blood serum, which comprises subjecting body fluid complement to the action of an effective complement modulating amount of a compound of the above Formula I. Body fluids can include blood, plasma, serum, synovial fluid, cerebrospinal fluid, or pathological accumulations of fluid such as pleural effusion, etc. This invention also concerns a method of modulating the complement system in a warm-blooded animal which comprises administering to said warm-blooded animal an effective complement modulating amount of a compound of the above Formula I.

In addition, this invention is concerned with the precursors in the preparation of the complement modulating compounds of Formula I, shown by the following Formula II:

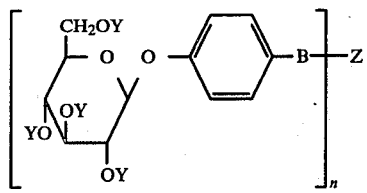

wherein Y is selected from the group consisting of —H and —COCH$_3$ and B, Z and n are as defined in Formula I.

Specific compounds of Formula II which are of particular interest as intermediates for the production of the compounds of Formula I include the following:

N,N',N''-tris[4-[(2,3,4,6-tetra-O-acetyl-β-D-glucopyranosyl)oxy]phenyl]-1,3,5-benzenetrisulfonamide N,N',N''-tris[4-[(β-D-glucopyranosyl)oxy]phenyl]-1,3,5-benzenetrisulfonamide Although the compounds of Formula I are shown as β-glycosides in the fully sulfated form, this invention also contemplates α-glycosides and partially sulfated α- and β-glycosides. This invention further contemplates other sugars such as aldo- or keto-hexoses or pentoses or uronic acids.

The compounds of Formula I find utility as complement modulators in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having nonimmunologic diseases such as paroxysmal nocturnal hemoglobinurea, hereditary angioneurotic edema and inflammatory states induced by the action of bacterial or lysosomal enzymes on the appropriate complement components as, for example, inflammation following coronary occlusion. They also may be useful in the treatment of transplant rejection and ulcers and as blood culture and transport mediums. The sulfated compounds of this invention such as the sodium and aluminum salts, may be particularly useful in the treatment of ulcers and the like on oral therapy. Also, the non-sulfated intermediate compounds of Formula II may be useful as immuno-enhancing agents or potentiators.

The compounds of this invention may be prepared according to the following flowchart.

FLOWCHART

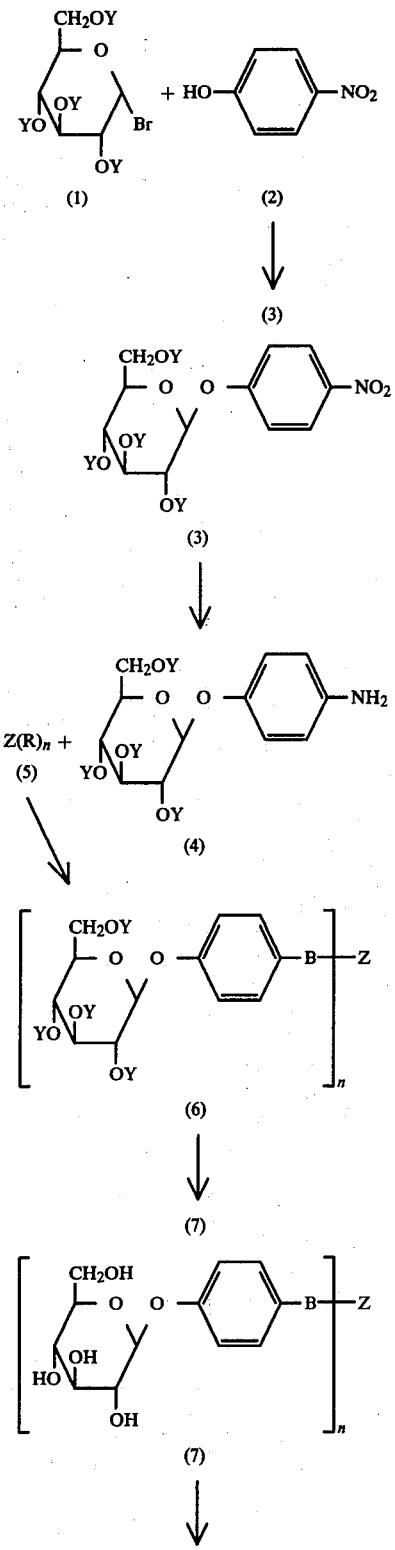

-continued
FLOWCHART

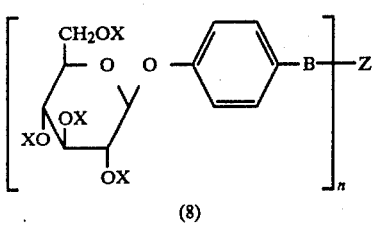

(8)

In accordance with the above flowchart an acetobromoglucose (1), where Y is —COCH₃, is reacted with sodium hydroxide in aqueous acetone and p-nitrophenol (2) for 18–36 hours, giving a 4-nitrophenyl 2,3,4,6-tetra-O-acetyl-α(or β)-D-glucopyranoside (3) which is then catalytically reduced to the corresponding 4-aminophenyl derivative (4) where Y remains —COCH₃ and then reacted with a di- or trisubstituted arylene compound (5), where Z is as described hereinbefore, R is —COCl or —SOOCl and n is an integer 2 or 3, giving an N,N'-(or N,N',N"-)bis(or tris)-[4-[(2,3,4,6-tetra-O-acetyl-α(or β)-D-glucopyranosyl)oxy]phenyl]di-(or tri-)substituted arylene carboxamide (or sulfonamide) (6), where Y is —COCH₃ and B, Z and n are as hereinbefore described. The tetraacetyl derivative (6) is then reacted with sodium in methanol under an inert atmosphere for 1–4 hours, giving (7). Derivative (7) is then reacted first with a trialkylamine (C₁–C₆) sulfur trioxide in N,N-dimethylacetamide for 18–36 hours at 60°–85° C. and then added to acetone, giving a trialkylammonium (C₁–C₆) derivative (8), where X is —SO₃⁻NH⁺[alkyl (C₁–C₆)]₃, which is then reacted with a cation-containing compound wherein the salt forming moiety is selected from the group consisting of alkali metal, alkaline earth metal, aluminum, ammonia, zinc and substituted ammonia selected from the group consisting of piperidine, pyrazine, alkanolamine (C₂–C₆) and cycloalkylamine (C₃–C₆), and thereafter precipitated in ethanol, giving the end product (8) of this invention, where B, Z and n are as described above and X is —SO₃M where M is as described above.

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, thin-layer chromatography, distillation, etc. Also it should be appreciated that when typical reaction conditions (e.g., temperatures, mole ratios, reaction times) have been given, the conditions which are both above and below these specified ranges can also be used, though generally less conveniently.

The term "pharmaceutically acceptable salt" refers to those salts of the parent compound which do not significantly or adversely affect the pharmaceutical properties (e.g., toxicity, effectiveness, etc.) of the parent compound. The salt forming moieties of the present invention which are pharmaceutically acceptable include the alkali metals (e.g., sodium, potassium, etc.); alkaline earth metals (e.g., calcium, etc.); aluminum; zinc; ammonia; and substituted ammonia selected from the group consisting of trialkylamine (C₁–C₆), piperidine, pyrazine, alkanolamine (C₂–C₆) and cycloalkylamine (C₃–C₆).

The term "trialkylamine (C₁–C₆)" defines those amines having three aliphatic fully saturated hydrocarbon substituents containing 1 to 6 carbon atoms either linearly or branched. Typically, these amines are trimethylamine, triethylamine, tripropylamine, dimethylethylamine, dimethyl-1-propylamine, etc. The term "alkanolamine (C₂–C₆)" refers to the above-defined trialkylamines additionally substituted with at least one and not more than three hydroxy groups on at least two of the alkyl hydrocarbon chains. Such amines are, for example, triethanolamine, tripropanolamine, etc. The term "cycloalkylamine (C₃–C₆)" is defined as the 3 to 6 fully saturated carbocyclic moieties such as cyclopropyl, methylcyclobutyl, cyclopentyl, cyclohexyl, etc.

As used hereinabove and below unless expressly stated to the contrary, all temperatures and temperature ranges refer to the centigrade system and the terms "ambient" or "room temperature" refer to about 25° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

Whereas the exact scope of the instant invention is set forth in the appended claims, the following specific examples illustrate certain aspects of the present invention. However, the examples are set forth for illustration only and are not to be construed as limitations on the present invention except as set forth in the appended claims.

A further understanding of the invention can be obtained from the following non-limiting Preparations and Examples.

EXAMPLE 1

4-Aminophenyl (2,3,4,6-tetra-O-acetyl)-β-D-glucopyranoside

To a mixture of 15 g of acetobromoglucose, 7.92 g of sodium 4-nitrophenolate and 50 ml of acetone was added 300 mg of sodium hydroxide in 15 ml of water. This mixture was stirred for 18 hours, poured into 400 ml of water and the precipitate was filtered off. The residue was dissolved in 200 ml of methylene chloride, washed with 100 ml of aqueous sodium bicarbonate solution, dried and passed through a pad of hydrous magnesium silicate. Evaporation of the solvent and crystallization yielded 4.26 g of 4-nitrophenyl (2,3,4,6-tetra-O-acetyl)-β-D-glucopyranoside as white crystals, mp 173°–175° C.

A 2.65 g sample of the above product was dissolved in 50 ml of acetic acid and hydrogenated in the presence of 300 mg of 10% palladium-on-carbon catalyst until hydrogen up-take stopped. The solution was filtered through diatomaceous earth and evaporated. The residue was evaporated twice from 100 ml portions of toluene and crystallized from ethanol to yield 2.50 g of the title compound, mp 130°–133° C.

EXAMPLE 2

N,N',N"-Tris[4-[(2,3,4,6-tetra-O-acetyl-β-D-glucopyranosyl)oxy]phenyl]-1,3,5-benzenetrisulfonamide A mixture of 2.0 g of 4-aminophenyl 4-O-(2,3,4,6-tetra-O-acetyl)-β-D-glucopyranoside, 570 mg of 1,3,5-benzenetrisulfonyl chloride and 10 ml each of dry pyridine and dry acetonitrile was stirred for 22 hours, then diluted with 100 ml of water and extracted with three 50 ml portions of dichloromethane. The extracts were combined, washed twice with 50 ml of 0.5 N hydrochloric acid, then once with brine, dried and filtered through hydrous magnesium silicate. The solvents were evaporated giving a tan foam which was the desired intermediate.

EXAMPLE 3

N,N',N''-Tris[4-[($\beta$-D-glucopyranosyl)oxy]phenyl]-1,3,5-benzenetrisulfonamide To a solution of 1.8 g of N,N',N''-tris[4-[(2,3,4-6-tetra-O-acetyl-$\beta$-D-glucopyranosyl)oxy]phenyl]-1,3,5-benzenetrisulfonamide in 20 ml of methanol was added 105 mg of sodium metal. The mixture was allowed to stand 2 hours, the solvent was evaporated, the oily residue was taken up in 20 ml of water and then passed through a 15 mm (inside diameter) column containing 25 g. of Amerlite ® IR-20 ion exchange resin which had been activated by washing with concentrated hydrochloric acid, then water to neutrality. The product was washed from the column after 5 minutes with 50 ml of water which was then evaporated, giving a foam. This foam was dissolved in water and passed through a column of 200 g of Sephadex ® G-25, giving, after crystallization from isopropanol, 0.79 g of the desired intermediate as a white powder, mp 187°–190° C.

EXAMPLE 4

Dodecasodium N,N',N''-tris[4-[(2,3,4,6-tetra-O-sulfo-$\beta$-D-glucopyranosyl)oxy]phenyl]-1,3,5-benzenetrisulfonamide A mixture of 500 mg of N,N',N''-tris[4-[($\beta$-D-glucopyranosyl)oxy]phenyl]-1,3,5-benzenetrisulfonamide, 2.02 g of triethylamine sulfurtrioxide complex, 2.0 g of 3 Å molecular sieves and 10 ml of dry N,N-dimethylacetamide was stirred under argon at 80° C. for 48 hours, then cooled and filtered into 300 ml of stirred acetone. After standing one hour the supernatant was filtered through diatomaceous earth, while the residual oil was saved. The diatomaceous earth, containing dodecatriethylammonium N,N',N''-tris[4-[(2,3,4,6-tetra-O-sulfo-$\beta$-D-glucopyranosyl)oxy]phenyl]-1,3,5-benzenetrisulfonamide was washed with 5 ml of 30% aqueous sodium acetate, then 10 ml of water. The combined wash was added to the oil (saved above) and then 500 ml of ethanol was added giving a solid which was collected and dried, giving 1.07 g of the desired product as a cream colored powder $[\alpha]_D^{26} -25° \pm 1$ (0.807% water).

EXAMPLE 5

Preparation of Compressed Tablet

| Ingredient | mg/Tablet |
| --- | --- |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 6

Preparation of Compressed Tablet—Sustained Action

| Ingredient | mg/Tablet |
| --- | --- |
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 7

Preparation of Hard Shell Capsule

| Ingredient | mq/Capsule |
| --- | --- |
| Active Compound | 0.5–500 |
| Lactose, Spray Dried | qs |
| Magnesium Stearate | 1–10 |

EXAMPLE 8

Preparation of Oral Liquid (Syrup)

| Ingredient | % W/V |
| --- | --- |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 9

Preparation of Oral Liquid (Elixir)

| Ingredient | % W/V |
| --- | --- |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

Example 10

Preparation of Oral Suspension (Syrup)

| Ingredient | % W/V |
| --- | --- |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 11

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 12

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 13

Preparation of Intra-Articular Product

| Ingredient | Amount |
|---|---|
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 14

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 15

Preparation of Dental Paste

| Ingredient | % W/V |
|---|---|
| Active Compound | 0.05–5 |
| Zinc Oxide | 15 |
| Polyethylene Glycol 4000 USP | 50 |
| Distilled Water qs | 100 |

EXAMPLE 16

Preparation of Dental Ointment

| Ingredient | % W/W |
|---|---|
| Active Compound | 0.05–5 |
| Petrolatum, White USP qs | 100 |

EXAMPLE 17

Preparation of Dental Cream

| Ingredient | % W/W |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 18

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Parabeh USP | 0.02 |
| Purified Water qs | 100 |

EXAMPLE 19

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 20

Preparation of Spray Lotion (Non-aerosol)

| Ingredient | % W/W |
|---|---|
| Active Compound | 0.05–5 |
| Isopropyl Myristate | 20 |
| Alcohol (Denatured) qs | 100 |

EXAMPLE 21

Preparation of Buccal Tablet

| Ingredient | mg/Tablet |
|---|---|
| Active Ingredient | 3.25 |
| 6 × Sugar | 290.60 |
| Acacia | 14.53 |
| Soluble Starch | 14.53 |
| F.D. & C. Yellow No. 6 Dye | 0.49 |
| Magnesium Stearate | 1.60 |
| | 325.00 |

The final tablet will weigh about 325 mg and may be compressed into buccal tablets in flat faced or any other tooling shape convenient for buccal administration.

EXAMPLE 22

Preparation of Lozenge

| Ingredient | g/Lozenge |
| --- | --- |
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝″ flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint/week may be used, with proportionally smaller doses for smaller joints. the dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form", as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement modulating activity of compounds of this invention has been demonstrated by the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; and (ii) Test Code 035 (C3–C9 inhibitor)—This test determines the ability of the late components of human complement (C3–C9) to lyse EAC 142 in the presence of appropriate dilutions of the test compound. An active inhibitor protects EAC 142 from lysis by human C3–C9. The results of Test Code 026 and 035 appear in Table I showing that the principal compound of the invention possesses highly significant complement modulating activity in warm-blooded animals.

TABLE I

| | Biological Activities | |
| --- | --- | --- |
| Compound | C-1 026* Wells | C-Late 035* Wells |
| Dodecasasodium N,N',N''—tris[4-[(2,3,4,6- | 9** | 2 |

TABLE I-continued

| | Biological Activities | |
|---|---|---|
| Compound | C-1 026* Wells | C-Late 035* Wells |
| tetra-O—sulfo-β-D-glucopyranosyl)oxy]-phenyl]-1,3,5-benzenetrisulfonamide | | |

*Tests identified by code herein. For a discussion of the tests, see "Systematic Discovery & Evaluation of Complement Inhibitors", N. Bauman et al., Immunopharmacology 3:317-24 (1981).
**Activity in wells, a serial dilution assay; higher well number indicates higher activity. The serial dilutions are two-fold.

We claim:

1. A compound selected from those of the formula:

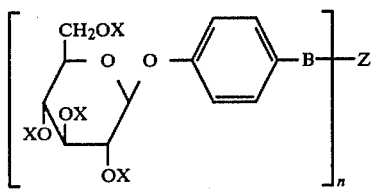

wherein X is —SO$_3$M and M is a nontoxic pharmaceutically acceptable cation salt, wherein the salt forming moiety is selected from the group consisting of alkali metal, alkaline earth metal, aluminum, ammonia, zinc and substituted ammonia selected from the group consisting of trialkylamine (C$_1$-C$_6$), piperidine, pyrazine, alkanolamine (C$_2$-C$_6$) and cycloalkylamine (C$_3$-C$_6$); B is selected from the group consisting of —NHCO— and —NHSO$_2$—; n is an integer 2 or 3; and Z is an arylene selected from the group consisting of:

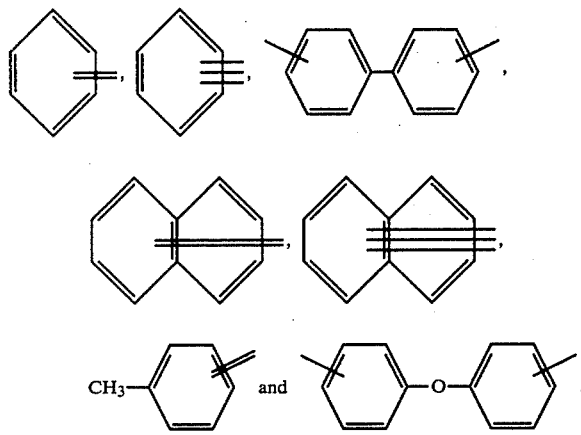

2. The compound according to claim 1, dodecatriethylammonium N,N',N''-tris[4-[(2,3,4,6-tetra-O-sulfo-β-D-glucopyranosyl)oxy]phenyl]-1,3,5-benzenetrisulfonamide, where the structure is:

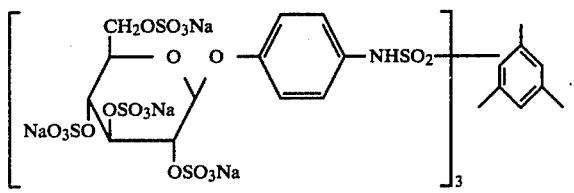

wherein A is N$^+$H(C$_2$H$_5$)$_3$.

3. The compound according to claim 1, dodecasodium N,N',N''-tris[4-[(2,3,4,6-tetra-O-sulfo-β-D-glucopyranosyl)oxy]phenyl]-1,3,5-benzenetrisulfonamide, where the structure is:

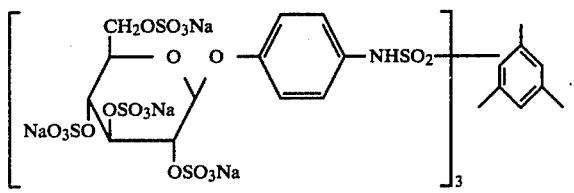

4. A compound selected from those of the formula:

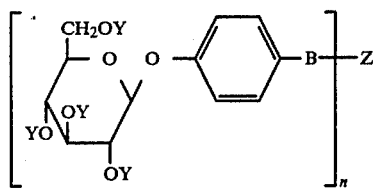

wherein Y is selected from the group consisting of H and —COCH$_3$; B is selected from the group consisting of —NHCO— and —NHSO$_2$—; n is an integer 2 or 3; and Z is an arylene selected from the group consisting of:

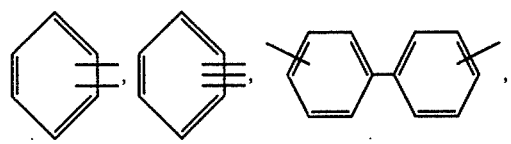

5. The compound according to claim 4, N,N',N''-tris[4-[(2,3,4,6-tetra-O-acetyl-β-D-glycopyranosyl)oxy]phenyl]-1,3,5-benzenetrisulfonamide, where the structure is:

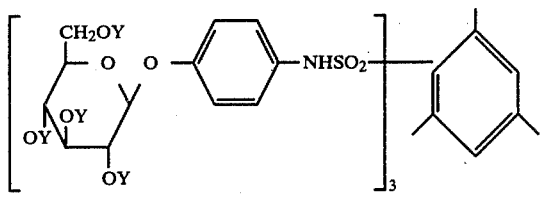

wherein Y is —COCH$_3$.

6. The compound according to claim 4, N,N',N''-tris[4-[(β-D-glucopyranosyl)oxy]phenyl]-1,3,5-benzenetrisulfonamide, where the structure is:

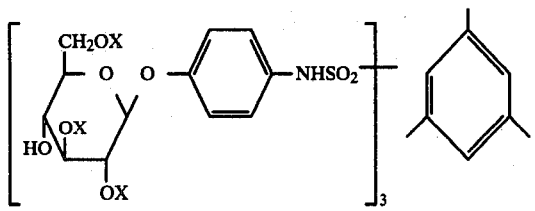

7. A method of modulating the complement system in a body fluid which comprises subjecting said body fluid to the action of an effective complement modulating amount of a pharmaceutically acceptable compound selected from those of the formula:

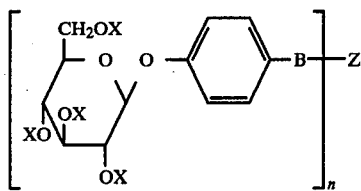

wherein X is —$SO_3M$ and M is a nontoxic pharmaceutically acceptable cation salt, wherein the salt forming moiety is selected from the group consisting of alkali metal, alkaline earth metal, aluminum, ammonia, zinc and substituted ammonia selected from the group consisting of trialkylamine ($C_1$-$C_6$), piperidine, pyrazine, alkanolamine ($C_2$-$C_6$) and cycloalkylamine ($C_3$-$C_6$); B is selected from the group consisting of —NHCO— and —$NHSO_2$—; n is an integer 2 or 3; and Z is an arylene selected from the group consisting of:

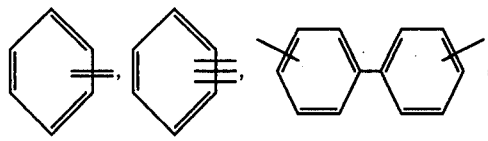

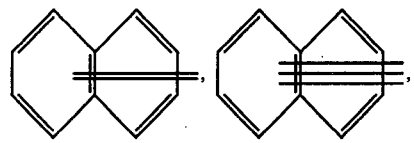

8. The method according to claim 7, wherein the body fluid is blood serum.

9. The method according to claim 7, wherein the compound is dodecatriethylammonium N,N',N''-tris[4-[(2,3,4,6-tetra-O-sulfo-β-D-glucopyranosyl)oxy]-phenyl]-1,3,5-benzenetrisulfonamide.

10. The method according to claim 7, wherein the compound is dodecasodium N,N',N''-tris[4-[(2,3,4,6-tetra-O-sulfo-β-D-glucopyranosyl)oxy]phenyl]-1,3,5-benzenetrisulfonamide.

11. A method of modulating the complement system in a warm-blooded animal which comprises administering to said warm-blooded animal an effective complement modulating amount of a pharmaceutically acceptable compound selected from those of the formula:

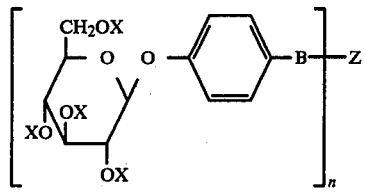

wherein X is —$SO_3M$ and M is a nontoxic pharmaceutically acceptable cation salt, wherein the salt forming moiety is selected from the group consisting of alkali metal, alkaline earth metal, aluminum, ammonia, zinc and substituted ammonia selected from the group consisting of trialkylamine ($C_1$-$C_6$), piperidine, pyrazine, alkanolamine ($C_2$-$C_6$) and cycloalkylamine ($C_3$-$C_6$); B is selected from the group consisting of —NHCO— and —$NHSO_2$; n is an integer 2 or 3; and Z is an arylene selected from the group consisting of:

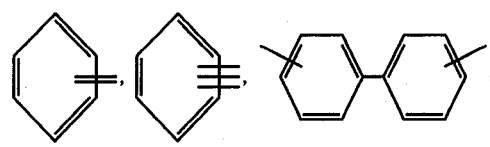

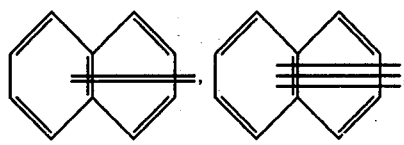

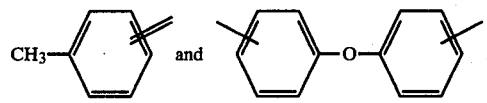

12. The method according to claim 11, wherein the compound is dodecatriethylammonium N,N',N''-tris[4-[(2,3,4,6-tetra-O-sulfo-β-D-glucopyranosyl)oxy]-phenyl]-1,3,5-benzenetrisulfonamide.

13. The method according to claim 11, wherein the compound is dodecasodium N,N',N''-tris[4-[(2,3,4,6-tetra-O-sulfo-β-D-glucopyranosyl)oxy]phenyl]-1,3,5-benzenetrisulfonamide.

14. The method according to claim 11, wherein the compound is administered internally.

15. The method according to claim 11, wherein the compound is administered topically.

16. The method according to claim 11, wherein the compound is administered periodontally in the oral cavity.

17. The method according to claim 11, wherein the compound is administered intra-articularly.

18. The method according to claim 11, wherein the compound is administered parenterally.

* * * * *